US United States Patent [19]
Christidis

[11] 3,954,874
[45] May 4, 1976

[54] PROCESS OF MANUFACTURE OF POLYHYDRIC ALCOHOL BROMOHYDRINS
[75] Inventor: Yani Christidis, Paris, France
[73] Assignee: Nobel Hoechst Chimie, Puteaux, France
[22] Filed: Aug. 13, 1974
[21] Appl. No.: 497,044

[30] Foreign Application Priority Data
Aug. 23, 1973  France .............................. 73.30588

[52] U.S. Cl. ...................... 260/584 R; 260/488 F; 260/633; 260/488 J
[51] Int. Cl.$^2$ .................. C07C 91/00; C07C 31/34
[58] Field of Search ............. 260/633, 488 J, 488 F, 260/584 R

[56]         References Cited
         UNITED STATES PATENTS
2,144,612    1/1939    Britton et al. ....................... 260/633
2,198,600    4/1940    Britton et al. ....................... 260/633
2,763,679    6/1956    Dee ................................ 260/633 X FOREIGN PATENTS OR APPLICATIONS
935,362    10/1955    Germany .......................... 260/633

OTHER PUBLICATIONS
Bayaert et al., Natuar weten Schappelijt tijdschrift 22, 249–262, (1940).

Saucier et al., Canadian J. Chem. 44, (13), (1966), pp. 1599–1601.
Geiseler et al., Z. Natur. 22A, (1967), pp. 1511–1516.

Primary Examiner—Howard T. Mars
Attorney, Agent, or Firm—Karl W. Flocks

[57]            ABSTRACT

An improvement to the process for preparing a polyhydric alcohol bromohydrin from the group consisting in the polymethylol-alkanes, penta-erythritols, amino-substituted polyhydric alcohols by the action of hydrobromic acid on the said polyhydric alcohol, consisting of effecting the reaction in an acetic medium with an aqueous solution of hydrobromic acid, eliminating the water during the course of the reaction by distillation of a water-acetic acid mixture rich in water, by means of an apparatus comprising a distillation column adapted to extract vapours at a temperature lower than 103°C, collecting the resultant product, subjecting this latter to a transesterification reaction with a monohydric-alcohol of low molecular weight from the methanol group, and subjecting said product to a purification treatment.

9 Claims, No Drawings

PROCESS OF MANUFACTURE OF POLYHYDRIC ALCOHOL BROMOHYDRINS

The present invention relates to a process of manufacture of bromohydrins of polyhydric alcohols.

It is known to prepare the bromohydrins of polyhydric alcohols and especially of polymethylol-alkanes by the replacement of part or the whole of their hydroxyl groups by atoms of bromine by means of hydrobromic acid, following the general diagram below:

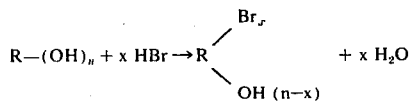

where $X$ is lower than or equal to $n$.

In order to obtain suitable yields, especially during the preparation of highly brominated compounds, this reaction must be carried out under pressure or in an anhydrous medium, either with gaseous HBr or in the presence of compounds capable of fixing the water of reaction such as acetic anhydride or acetyl chloride. Now, the use of pressure or anhydrous reactants is expensive and complicates the manufacture; in addition, the known methods frequently provide impure products caused by secondary reactions.

Acetic acid is very often used as the solvent in this type of reaction, but the use at the same time of acetic acid and an aqueous solution of hydrobromic acid does not make it possible to obtain satisfactory yields in view of the difficulty of eliminating during the course of the reaction, the water brought-in by the reactants and the water formed, without at the same time eliminating the hydrobromic acid.

It has been found possible to manufacture the bromohydrins of polyhydric alcohol of satisfactory purity with excellent yields by the action of aqueous hydrobromic acid on polyhydric alcohol in an acetic medium at atmospheric pressure, by eliminating during the course of the reaction, in the form of an acetic acid-water mixture, without loss of hydrobromic acid, the greater part of the water brought-in by the reactants and the reaction water, by providing on the reactor a distillation column enabling vapours to be extracted at a temperature not exceeding 103°C. It has in fact been found that under these conditions, the vapours extracted contain practically no hydrobromic acid.

The distillation column used may either be a column with filling elements or any other type of column equipped or not with an automatic device permitting the regulation of the rate of reflux, provided that it is sufficiently powerful to permit the extraction of the vapours at a temperature not exceeding 103°C.

In the process according to the invention, aqueous hydrobromic acid is thus caused to react on polyhydric alcohol in an acetic medium, either in the theoretical quantity or in excess, depending on the bromine derivative which it is mainly desired to obtain, in a reactor provided with a column, and the heating is regulated in such manner that the temperature of extraction of the distillate vapours does not exceed 103°C.

When the temperature exceeds 103°C, it is desirable to stop the extraction of the distillate and to re-start it only when the temperature of the vapours has again fallen below 103°C. Under these conditions, the water is gradually eliminated in the form of a distillate constituted by a mixture of water and acetic acid rich in water, and there is no loss of hydrobromic acid.

The acetic acid increases the solubility of the hydrobromic acid in the medium and facilitates the elimination of water.

As the reaction takes place in an acetic medium, the hydroxyl functions not replaced by atoms of bromine are in the form more or less completely acetylated at the end of the reaction, and they are liberated by transesterification with a monohydric alcohol, preferably of low molecular weight, such as methanol.

The process of the invention is applicable to all polyhydric alcohols and more particularly to polymethylol-alkanes such as trimethylol-ethane, trimethylol-propane, penta-erythritol, dipenta-erythritol, etc., and also to polyhydric alcohols comprising other reactant groups, for example to the polyhydric alcohols comprising a primary amine group such as trimethylol-amino-methane which is then obtained in the form of hydrobromide of bromo-hydrin.

The invention also covers accessorily an economic method of purification of tribromo-hydrin of penta-erythritol which consists essentially of pouring with powerful stirring, after concentration, the methanol solution of transesterification into water kept at a temperature somewhat lower tha the melting point of the mixture to be purified. Under these conditions, the tribromo-hydrin precipitates in the practically pure state, while the other constituents of the mixture, especially di-bromohydrine, remain in solution.

The process according to the invention enables high yields to be obtained, while consuming a quantity of hydrobromic acid close to the theoretical amount. The duration of the reaction is substantially shorter than in known methods. In addition, the method of operation is simple and easy to apply industrially. The products obtained contain little impurities and the process is therefore economical.

The bromo-hydrins of polyhydric alcohols thus prepared have numerous applications as fireproofing compounds in polyesters and polyurethanes. When they still contain reactant groups such as OH groups, they are utilized as intermediaries in the synthesis of other fireproofing compounds, for example of phosphorated derivatives employed in various industries.

The examples given below have the object of illustrating the invention but they do not constitute any limitation. They have been carried out with 62% aqueous hydrobromic acid; the same results are obtained with 48% acid, with a prolongation of the duration of the reactions.

EXAMPLE 1

Preparation of dibromo-hydrin of penta-erythritol

In a three-necked flask of 8 liters, provided with a stirring device, a dropping-funnel, a fractionating column of 600 mm. useful height and 40 mm. internal diameter, filled with Raschig rings and equipped with a column head permitting manual regulation of the reflux rate, followed by a condenser, there are charged:

| | |
|---|---|
| An aqueous solution of 62% hydrobromic acid | 5320 grams (40 mols) |
| Penta-erythritol | 2720 grams (20 mols) |
| Acetic acid | 600 grams (10 mols) |

The reaction mixture is brought to boiling point while stirring. As soon as the boiling is established and the vapours reach the head of the column, there is observed a temperature of 121.5°C. in the reaction mixture and 100°–101°C. at the head of the column. The speed of distillation is regulated in such manner as not to exceed a temperature of 103°C. at the head of the column. At the end of 5 hours, the temperature rises abruptly in the reaction medium since there are no more acids in the flask; the hydrobromic acid has completely reacted with the penta-erythritol. A part of the acetic acid has distilled, in a mixture with water, in the form of a mixture with about 80% of water, the remainder being bound to the penta-erythritol in the form of acetate.

In order to free the brominated penta-erythritol which is present in the form of acetate, a transesterification is effected by methanol. For this purpose, after cooling, there are added 2 liters of methanol and a catalytic quantity of 62% hydrobromic acid, after which the whole is brought-up to boiling with reflux. A mixture of methanol and methyl acetate is then distilled.

When the temperature at the head of the column corresponds to the boiling point of the methanol (65°C.) the mixture is cooled, neutralized with a 4N methanol solution of ammonia and 160 grams of activated carbon is added.

The mixture is brought-up to boiling with reflux for 45 minutes and is then filtered while hot on a filtration aid (Clarcel).

The slightly yellow filtrate is then concentrated to dry; practically the whole of the methanol used is then recovered.

There are obtained 4995 grams of crude products, the composition of which, determined by chromatography in the vapour phase, is as follows:

| | |
|---|---|
| Heads + mono-bromohydrin | 2.0% |
| Dibromo-hydrin | 84.0% |
| Tribromo-hydrin | 14.0% | or a total of 4195 grams (16 mols) of dibromo-hydrin (yield 80.5%) and 699 grams (2.15 mols) of tribromo-hydrin. The yield of di- and tribromo-hydrin with respect to the penta-erythritol is 90.7% and, with respect to the hydrobromic acid, 98.6%.

The crude product is re-crystallized from trichloro-ethylene; there are obtained 3945 grams of dibromo-hydrin at 97% purity, or a yield of 75% of dibromo-hydrin, and there are recovered by evaporation of the trichloro-ethylene 1030 grams of a product containing 68 to 70% of tribromo-hydrin, the remainder being essentially dibromo-hydrin which can easily be converted in its totality to tribromo-hydrin.

Characteristics of re-crystallized dibromo-hydrin:

| | |
|---|---|
| Melting point | 109°C. |
| Boiling point | 320°C. at 760 mm. of mercury; |
| Apparent density | 1.1 – 1.2. |

EXAMPLE 2

Preparation of tribromo-hydrin of penta-erythritol

Into a flask of 6 liters, equipped as indicated for Example 1, there are charged:

| | |
|---|---|
| Aqueous solution of 62% | 4310 grams (33 mols) |
| hydrobromic acid | |
| Penta-erythritol | 1360 grams (10 mols) |
| Acetic acid | 1200 grams (20 mols). |

The mixture is brought-up to boiling point as in Example 1 and is distilled, keeping the temperature below 103°C. at the head of the column.

At the end of 13 hours, there are collected 2652 grams of distillate containing 18 to 20% of acetic acid. During the course of the reaction, it is found that when about 2000 grams of distillate have been eliminated, there is produced a fresh release of the tribromo-hydrin. The distillation is continued to a temperature of 129°–130°C. in the flask in order to eliminate the excess of hydrobromic acid.

A transesterification is then carried out in order to liberate the brominated penta-erythritol. For this purpose, to the mixture cooled to 60°C. and dissolved in 3 liters of technical methanol, there are added 50 grams of 62% hydrobromic acid.

The mixture is again brought-up to boiling and a mixture of methanol and methyl acetate is distilled. The transesterification is terminated when the temperature at the head of the column is the boiling temperature of the methanol.

After cooling, the methanol solution is neutralized with ammonia and then treated with 78.6 grams of activated carbon (acticarbon 3 S) to reflux for 45 minutes. The solution is filtered while hot on the filtration aid "Clarcel", and the whole of the methanol is distilled.

There are thus obtained 3140 grams of a crude almost colourless product having the following composition:

| | |
|---|---|
| Monobromo-hydrin | 1.0% |
| Dibromo-hydrin | 8.0% |
| Tribromo-hydrin | 91.0% | or a yield of 87.9% of tribromo-hydrin.

The crude product may be purified, for example by carrying out the extraction with water of a solution in trichloro-ethylene. The tribromo-hydrin is in fact wholly insoluble in water.

2810 grams of crude product are dissolved in 11,135 grams (7650 cu.cm.) of trichloro-ethylene. The solution obtained is extracted with 22 to 24 liters of water at 50°–55°C., and then the last traces of water in the solution in trichloroethylene are azeotropically eliminated by boiling the solution. After cooling to 20°C., there is obtained a first fraction of 825 grams of tribromo-hydrin with a purity of 99.4% by chromatography in the vapour phase. The filtrate concentrated to half gives a second fraction of 645 grams at 99.5% and finally a third fraction of 600 grams at 99.3%, or a total of 2070 grams.

The yield of the re-crystallization is 73.5%. After recovery of the trichloro-ethylene, the residue represents 366 grams. This is constituted by a mixture of di- and tribromo-hydrin which may be re-cycled to the preparation. The weight of the product extracted by water is 320 grams; this is essentially constituted by mono- and tribromo-hydrin and may also be re-cycled to the preparation. It is of course possible to utilize the same method of preparation with hydrobromic acid at 48%; the duration of the reaction would then only be slightly longer.

EXAMPLE 3

Preparation and purification of the tribromo-hydrin of penta-erythritol

The operation is carried out with the same charges as in Example 2, but in an apparatus comprising a slightly more powerful column. The temperature at the head of the column is held between 100° and 103°C.; the temperature in the reaction medium passes from 120°C. at the beginning to 125°C. at the end of the reaction.

Over a period of 14 hours there are distilled 2640 grams of 40% acetic acid. The heating is then increased in order to eliminate the excess of hydrobromic acid and the residual acetic acid; the temperature of the reaction medium reaches 150°C. After cooling to 80°C. there are added 3 liters of methanol and 50 cu.cm. of hydrobromic acid and the mixture is then brought to boiling point while distilling and there are thus recovered 640 cu.cm. of distillate containing 17% of methyl acetate and 83% of methanol.

After neutralization with ammonia, the methanol solution is treated with 62 grams of "Acticarbon LS" for 45 minutes to reflux, filtered while hot, and then the methanol is distilled in order to obtain a solution with 75% of dry matter. An aliquot part evaporated to the dry state gives a crude product containing:

| Impurities | 0.5% |
|---|---|
| Dibromo-hydrin | 5.2% |
| Tribromo-hydrin | 94.2% | by analysis by chromatography in the gaseous phase.

This cooled solution is poured while stirring vigorously into 8 liters of water while keeping the temperature at 44°–47°C. The tribromo-hydrin crystallizes in the form of fine crystals which are filtered on a Buchner filter or dried and which are washed with 2 liters of water at 35°–40°C.

The moist product is dried in a flow of air for 45 minutes at 30°–40°C.

There are thus obtained 2850 grams of tribromo-hydrin of penta-erythritol at a purity of 99.6% (0.3% of dibromo-hydrin) or a yield of 88% as compared with the theoretical value.

EXAMPLE 4

Preparation of tetrabromo-hydrin of dipenta-erythritol

Into a flask of 2 liters equipped in the same manner as in Example 1, there are charged:

| Dipenta-erythritol | 254 grams (1 mol) |
|---|---|
| Hydrobromic acid at 62% | 862 grams (6.6 mols) |
| Acetic acid | 240 grams (4 mols) |

The mixture is brought up to boiling with reflux which is maintained for 25 minutes, after which extraction of the distillate is begun. The temperature is then 123°C. in the flask and 98.5°C. in the vapours. The operation is continued for 10 hours 50 minutes without exceeding 103°C. in the vapours. There are collected 357 cu.cm. of a water-acetic acid mixture.

The heating is then increased and 335 cu.cm. of hydrobromic acid are distilled (120°C–121°C.). After cooling, 600 cu.cm. of methanol and 25 cu.cm. of 62% hydrobromic acid are added and brought up to boiling with reflux, after which 185 cu.cm. of a mixture of methanol and methyl acetate are distilled.

After neutralization of the residue with 100 cu.cm. of methanol ammonia 5N, there are added 18.7 grams (3%) of "Acticarbon LS" and the mixture is boiled for 45 minutes to reflux. The mixture is then filtered while hot on "Clarcel" and the solvent is stripped off under vacuum. The residue is treated with 500 cu.cm. of trichloro-ethylene and a little ammonium bromide is separated by filtration. After elimination of the solvent there are obtained 482.5 grams of a viscous coloured product, namely a yield of about 95% of crude product.

After re-crystallization in 400 cu.cm. of trichloroethylene, there is collected a first fraction of 396 grams of a white product constituted by tetrabromo-hydrin of dipentaerythritol.

| Br % | calculated: | 63.2% | found: | 62.8% |
|---|---|---|---|---|
| OH % | calculated: | 6.7% | found: | 6.3% |

EXAMPLE 5

Preparation of 2-amino-2-hydroxymethyl 1,3-dibromo-propane hydrobromide

Into a flask of 2 liters equipped like the apparatus of Example 1, there are introduced:

| trimethylol-amino-methane | 242 grams (2 mols) |
|---|---|
| Hydrobromic acid at 62% | 860 grams (6.6 mols) |
| Crystallized acetic acid | 300 grams (5 mols) |

The temperature rises to 78°-80°C. in the flask. The heating is continued up to boiling and is regulated in such manner as to obtain a temperature of 101°–103°C. at the head of the column, and collecting the distillate. In this way, there is eliminated in 18 hours, 490 grams of an aqueous liquid containing 18% of acetic acid.

The heating is then increased so as to distil the hydrobromic acid which has not reacted. Transesterification is then carried out by means of 600 cu.cm. of methanol containing 25 cu.cm. of hydrobromic acid at 62%. After elimination of the solvents, there is obtained a crude product which is recrystallized from isopropanol. The final product (540 grams) is constituted by 2-amino-2-hydroxymethyl-1,3-dibromo-propane. The yield is 82.5%.

It will of course be understood that the present invention has only been described purely by way of explanation and not in any restrictive sense and that any useful modification may be made thereto without departing from its scope as defined in the appended claims.

I claim:

1. In a process for preparing a polyhydric alcohol bromo-hydrin from the group consisting in the trimethylol-ethane, trimethylol-propane, penta-erythritol, dipenta-erythritol, and trimethylol-amino-methane by the action of an aqueous solution of hydrobromic acid on the said polyhydric alcohol in the presence of acetic acid, the improvement consisting in
    effecting the reaction with an aqueous solution of at least the theoretical amount of hydrobromic acid necessary to obtain said bromohydrin,
    eliminating the water during the course of the reaction by distillation of a water-acetic acid mixture rich in water while maintaining the distillation temperature no greater than 103°C.,
    collecting the resultant product, subjecting this latter to a transesterification reaction with methanol, and separating the resultant bromohydrin.

2. The improvement as claimed in claim 1, in which the concentration of the aqueous solution of hydrobromic acid is in the range from 45 to 65%.

3. The improvement as claimed in claim 2, in which the concentration of the said aqueous solution of hydrobromic acid is 48%.

4. The improvement as claimed in claim 2, in which the concentration of the aqueous solution of hydrobromic acid is 62%.

5. The improvement as claimed in claim 1, in which the reaction is carried out with penta-erythritol and with the theoretical quantity of hydrobromic acid, whereby there is obtained a main proportion of penta-erythritol dibromo-hydrin.

6. The improvement as claimed in claim 1, in which the reaction is carried out with penta-erythritol and with an excess of 10% of hydrobromic acid with respect to the theoretical quantity, whereby there is obtained a main proportion of penta-erythritol tribromo-hydrin.

7. The improvement as claimed in claim 1, in which the reaction is effected with dipenta-erythritol and with an excess of 65% of hydrobromic acid with respect to the theoretical quantity, whereby there is obtained a main proportion of dipenta-erythritol tetrabromo-hydrin.

8. The improvement as claimed in claim 1, in which the reaction is effected with trimethylol-aminomethane and with an excess of 10% of hydrobromic acid with respect to the theoretical quantity, whereby there is obtained a main proportion of 2-amino-2-hydroxymethyl-1,3-dibromo-propane.

9. The improvement as claimed in claim 1, in which the reaction is effected with penta-erythritol and with an excess of 10% of hydrobromic acid with respect to the theoretical quantity, and in which the resulting product is separated by a treatment comprising the concentration of the alcohol solution resulting from the transesterification and containing said product to be separated, the treatment of said resultant concentrated alcoholic solution while stirring by means of a large volume of water at a temperature slightly lower than the melting point of said product, the filtration and the drying of the resultant crystallized product, whereby there is obtained penta-erythritol tribromo-hydrin having a purity of at least 99%.

* * * * *